United States Patent
Berry

(10) Patent No.: US 8,039,252 B2
(45) Date of Patent: Oct. 18, 2011

(54) MULTI-CHAMBER CELL CULTURE ASSEMBLY

(76) Inventor: Eric Berry, Seabrook, NH (US)

(*) Notice: Subject to any disclaimer, the term of this patent is extended or adjusted under 35 U.S.C. 154(b) by 843 days.

(21) Appl. No.: 11/622,379

(22) Filed: Jan. 11, 2007

(65) Prior Publication Data

US 2007/0178583 A1  Aug. 2, 2007

Related U.S. Application Data

(60) Provisional application No. 60/758,016, filed on Jan. 11, 2006.

(51) Int. Cl.
 *C12M 1/22* (2006.01)
 *C12M 3/00* (2006.01)
 *C12M 1/34* (2006.01)

(52) U.S. Cl. ............. 435/305.2; 435/288.3; 435/288.5; 435/304.1; 435/305.1; 220/4.04; 220/4.26; 220/23.83; 220/507

(58) Field of Classification Search ............... 435/288.3, 435/288.5, 304.1, 305.1, 305.2, 4.04, 4.26, 435/23.83, 507
See application file for complete search history.

(56) References Cited

U.S. PATENT DOCUMENTS

| | | | |
|---|---|---|---|
| 4,654,308 A * | 3/1987 | Safi et al. | 435/294.1 |
| 4,661,458 A | 4/1987 | Berry et al. | |
| 5,240,854 A | 8/1993 | Berry et al. | |
| 5,272,084 A * | 12/1993 | O'Connell et al. | 435/395 |
| 5,744,366 A * | 4/1998 | Kricka et al. | 436/63 |
| 2004/0072347 A1* | 4/2004 | Schuler et al. | 435/372 |
| 2007/0026516 A1* | 2/2007 | Martin et al. | 435/297.5 |
| 2010/0216229 A1* | 8/2010 | Kenney et al. | 435/303.1 |

* cited by examiner

*Primary Examiner* — Nathan Bowers
(74) *Attorney, Agent, or Firm* — Grossman, Tucker, Perreault & Pfleger

(57) ABSTRACT

A multi-chamber cell culture assembly has provisions for the distribution of nutrient culture medium and gasses throughout each of the chambers. A device is constructed to provide a large surface area for the growth and cultivation of hybridomas, mammalian and insect cells. The device may incorporate macro, micro or nano structures on the growth surfaces to promote or enhance distribution of nutrients, cell product, gasses or growth area. Cell growth, nutrient addition and cell product withdrawal may be carried out automatically.

11 Claims, 9 Drawing Sheets

MULTI-CHAMBER CELL CULTURE ASSEMBLY

CROSS REFERENCE TO RELATED APPLICATIONS

The present application claims the benefit of the filing date of U.S. Provisional Application Ser. No. 60/758,016, filed Jan. 11, 2006, the teachings of which are incorporated herein by reference.

FIELD OF INVENTION

The present invention relates to a method and apparatus for the culture of cells.

BACKGROUND

Cell cultures provide for the growth and maintenance of a cell or cells in favorable conditions. Cells may include hybridomas, stem, mammalian and insect cells, among others. To grow and maintain the cells, cell nutrients, cell products and gasses may be provided to a culture.

SUMMARY

An exemplary aspect of the present invention relates to a cell growth chamber, the interior surfaces of which are adapted for the growth of cells and defining a culture space. An inlet may be defined in the cell growth chamber for providing fluid and gasses to the culture space and an outlet may be defined in the cell growth chamber for collecting the fluid and gasses from the culture space. The interior surfaces of the cell growth chamber may form a channel that is defined by a wall and a base located between said inlet and outlet.

One aspect of the present invention provides a cell culture device in which cells may be grown to a high density in a self contained apparatus.

Another aspect of the present invention provides a cell culture assembly having a plurality of growth chambers, wherein in each growth chamber may have a substantially equal distribution of nutrient medium and gasses.

Another aspect of the present invention provides a cell culture assembly that may allow for the continuous addition of nutrient medium and gasses and the removal of conditioned nutrient medium, gasses and products formed by the cells.

Another aspect of the present invention provides a flow system which may be continuous and may promote an optimal environment for the production of biochemicals, viral vaccines, antibodies and other pharmaceuticals.

Another aspect of the present invention provides a cell culture assembly that may be a self-contained device.

Another aspect of the present invention provides a cell culture assembly that may contain a variety of macro, micro and or nano structures, which may support or enhance the growth and attachment of cells and production of bio-chemicals.

BRIEF DESCRIPTION OF DRAWINGS

The detailed description below may be better understood with reference to the accompanying figures which are provided for illustrative purposes and are not to be considered as limiting any aspect of the invention.

DETAILED DESCRIPTION

The present invention may provide a culturing environment, which may be continuous, in a device having a plurality of growth chambers, stacked in an array, creating a large surface area for the culture of cells at high density, interspaced with a large surface area of nutrient medium exposed to the culture gasses. The device may be constructed and arranged to permit the directional flow of nutrient medium throughout each of the growth chambers. The flow may be adequate to provide for the gentle mixing of the nutrients throughout the entire growth area of the device, while at the same time providing adequate mixing with the culture gasses to assure that proper oxygenation and gas concentration may be maintained for the growth of cells.

Preferably, the culture device may include an array of culture chambers defined by the spaces between the superpositioning of a plurality of stacked plates. An inlet conduit may be provided for the nutrient medium. An inlet conduit may be provided for the introduction of culture gasses. The nutrient medium and the culture gasses may flow together throughout the culture chamber providing a distributed flow of nutrients mixed with the culture gasses throughout the entire growth chamber and each chamber may be serially connected to the next growth chamber. The growth surfaces of each of the culture chambers, may be altered by a variety of macro, micro or nano structures as required to effect the desired culture density or the proper distribution of gasified nutrient medium to either the basal or lateral surfaces of the cells being cultured.

Figure 1:
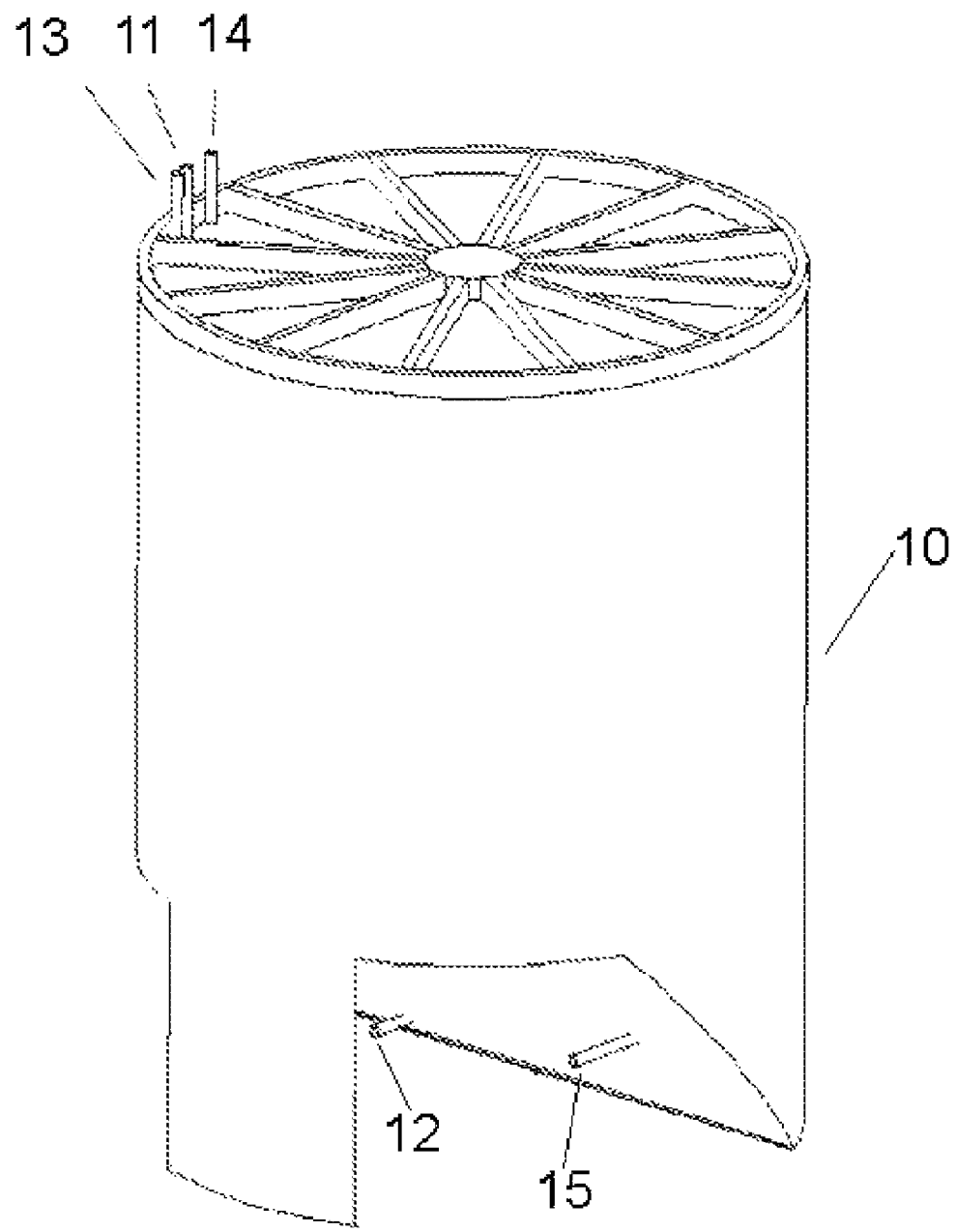
FIG. 1 is a perspective view of an exemplary embodiment of an assembly.
Figure 2:
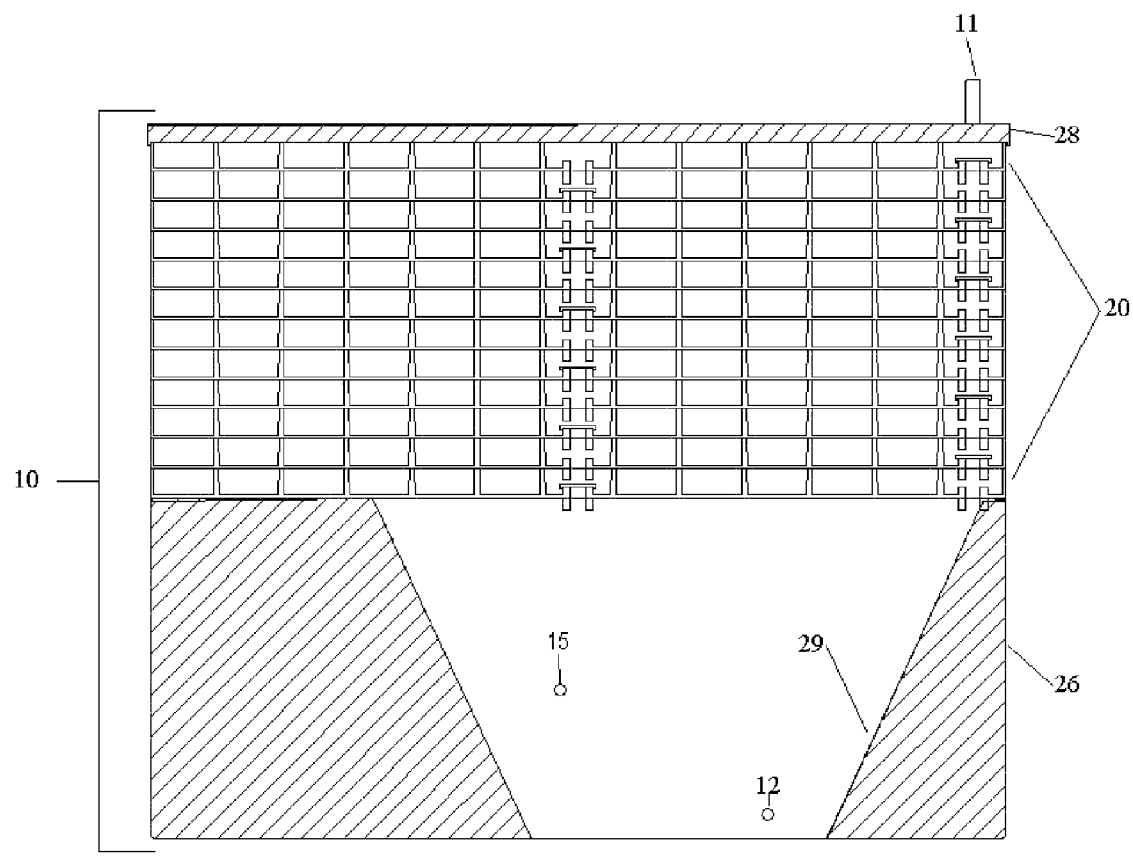
FIG. 2 is a cross sectional side view of an exemplary embodiment of an assembly.

The cell culture device of an exemplary embodiment may include an array of culture chambers enclosed within a vessel. The vessel may also incorporate a reservoir for the culture media and gasses. The exterior view, illustrated in FIG. 1, shows an exemplary embodiment of a vessel 10. The vessel 10 may be substantially cylindrical. The vessel 10 may incorporate as illustrated in FIG. 2 a molded top 28; a molded bottom reservoir 26 and culture chambers 20. The top 28, culture chambers 20, and bottom vessel 26, may be molded together or sealed to provide a fluid-tight arrangement for the culture chambers.

Referring back to FIG. 1, the vessel 10 may include three conduits extending from the top of the vessel 10; a fluid inlet conduit 11, a gas inlet conduit 13 and a gas outlet conduit 14. The bottom of the vessel may also contain two conduits, the fluid outlet conduit 12 and the product/waste conduit 15. Fluid may enter the vessel 10 through inlet conduit 11 and may flow gently down a fluid path of the first culture chamber 20. The fluid may form a stream of continuously moving and mixing fluid that may communicate with the cultured cells and may provide a continuous source of nutrients and gasses.

Figure 3:
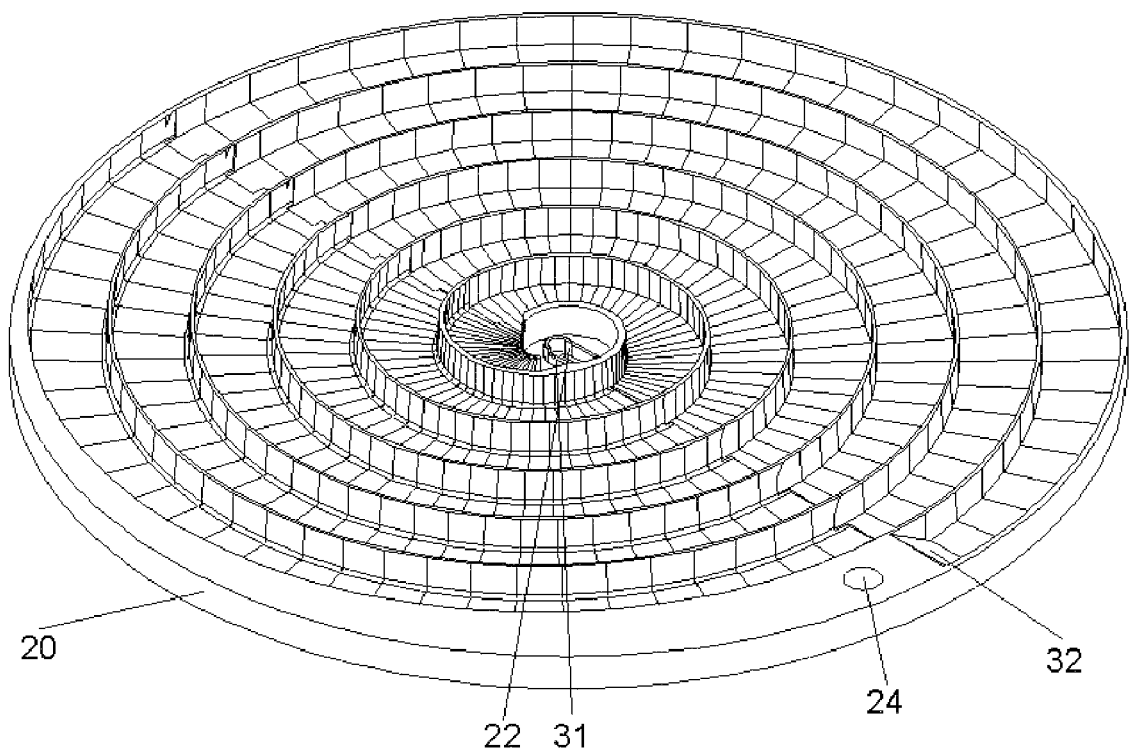
FIG. 3 is a perspective view of an exemplary plate of the assembly.

An exemplary embodiment of a single culture chamber is illustrated in FIG. 3. The fluid stream may enter the culture chamber at inlet 11 and flow down the sloped inlet path 32, moving through the structured culture chamber 20, and arriving at the outlet conduit 22 of the first culture chamber. The gas mixture may enter the first chamber from the gas inlet 13 and may then move throughout the entire culture chamber arriving at outlet 22.

Figure 6:
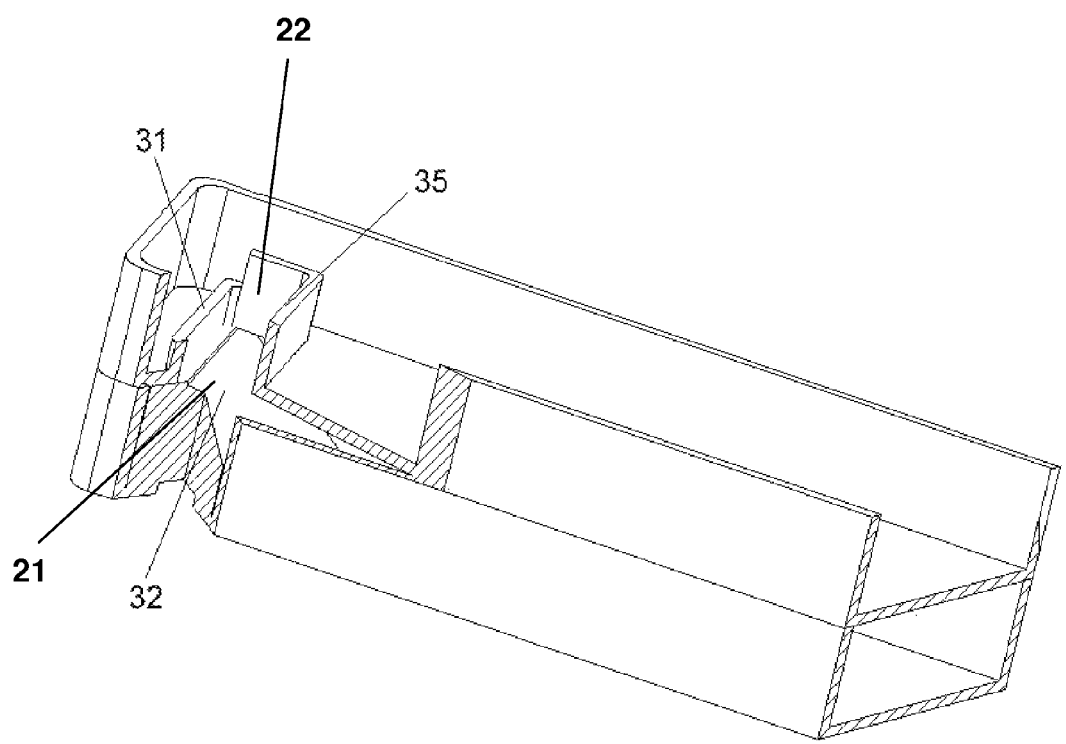
FIG. 6 is perspective view with section cut away to reveal an exemplary embodiment of interchamber fluid dams and fluid path.

A fluid dam 31, illustrated in FIG. 6, may be provided as a means to establish the depth of the fluid stream and may surround each outlet conduit 22. The depth of the fluid stream, may be varied to enhance the flow and mixing to the structured culture surface. The fluid may flow over the dam 31, and gently through the inlet conduit 21 and down the sloped inlet path 32 of inlet 21 of the next culture chamber FIG. 6. The gas dam 35, also illustrated in FIG. 6, may prevent the flow of fluids through a section of each outlet 22. The gasses may flow over the gas dam 35 through the inlet 21 of the next culture chamber. Each culture chamber 20 may contain a fluid dam 31 and a gas dam 35 located at the outlet of the culture chamber 22 and may include a sloped inlet path 32 located at the inlet 21 of the next culture chamber. The fluid path may repeat this process until it reaches the final outlet conduit 22 over the molded bottom reservoir 26, illustrated in FIG. 2. The fluid may flow gently down the reservoir inlet path 29 and may be collected in the reservoir 26.

The outlet conduits 12 and 15 may extend through the top of the assembly rather than through the base as shown in FIG. 2. Referring to FIG. 3, an exemplary culture chamber 20 of the array is depicted with the inlet conduit 21 covered to allow the flow of fluid to move axially towards the center of chamber 20 and over dam 31 of outlet conduit 22. The chamber 20 also affords a passage 24 for the egress of culture gasses collected and delivered to gas outlet conduit 14, illustrated in FIG. 1. Waste gasses that may be collected in the head space of the reservoir, may be collected and delivered via gas conduit 24 to the exit conduit 14, illustrated in FIG. 1.

Figure 4:
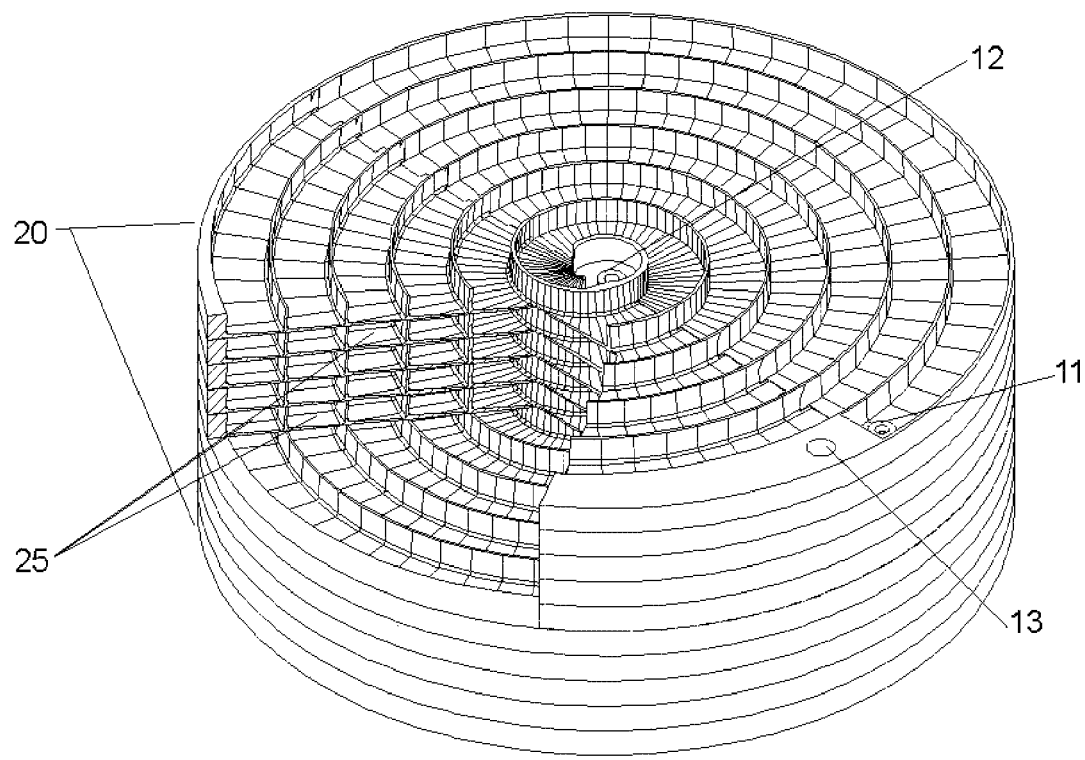
FIG. 4 is a perspective view of an exemplary array of plates sectioned to reveal the construction of the assembly.
Figure 5:
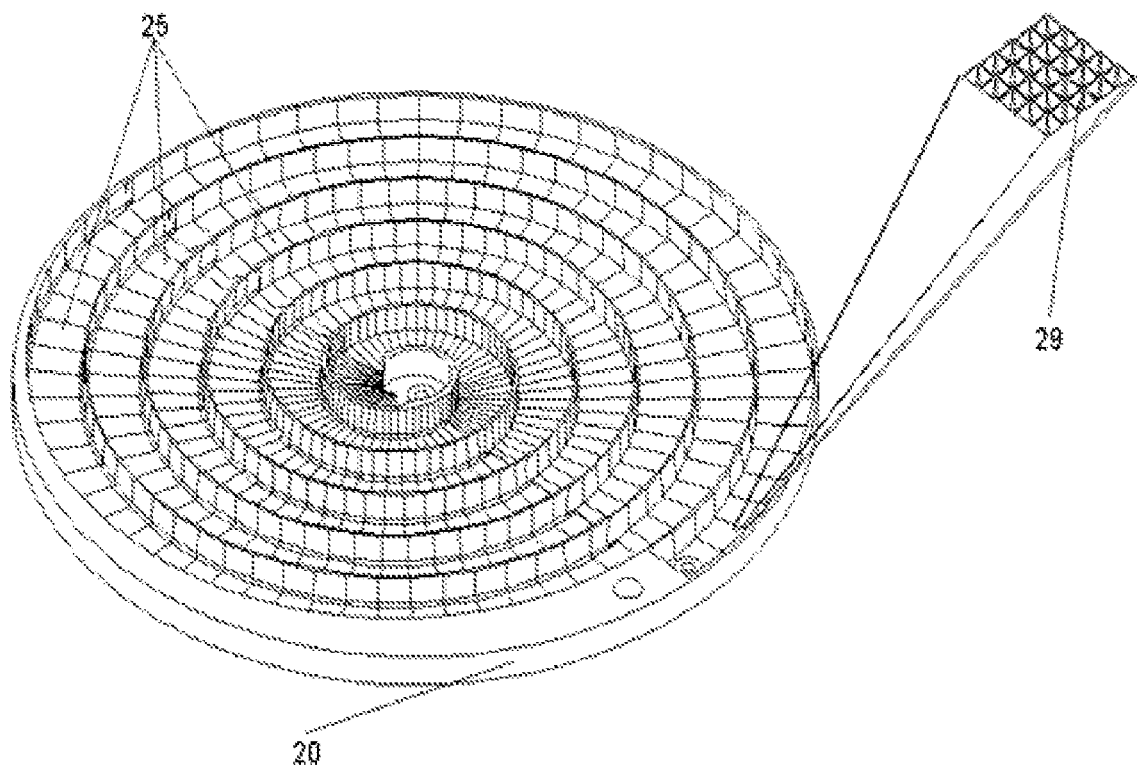
FIG. 5 is a perspective view of an exploded section of the structured surface of an exemplary growth area.

A large surface area of culture chambers may be provided by the superpositioning of culture chambers 20. Referring to FIG. 4, the section removed reveals culture spaces 25 formed by the superpositioning of chambers 20 in an array. Fluids retained in the culture chambers 20 may cover the culture surfaces 25. Referring to FIG. 5, the culture surfaces may be structured 29, illustrated in inset, to form either macro, micro or nano structures which may enhance the communication or distribution of nutrients or attachment sights within the culture chambers.

Figure 8:
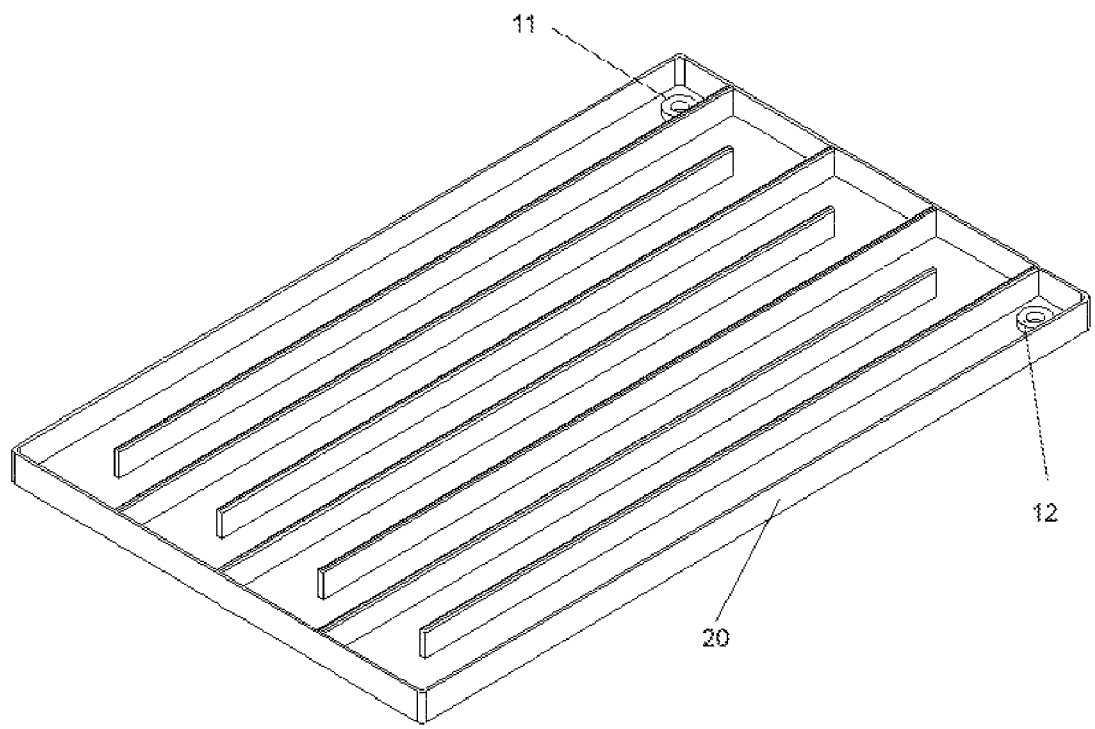
FIG. 8 is a perspective view of an exemplary plate of a rectangular embodiment of the invention.
Figure 9:
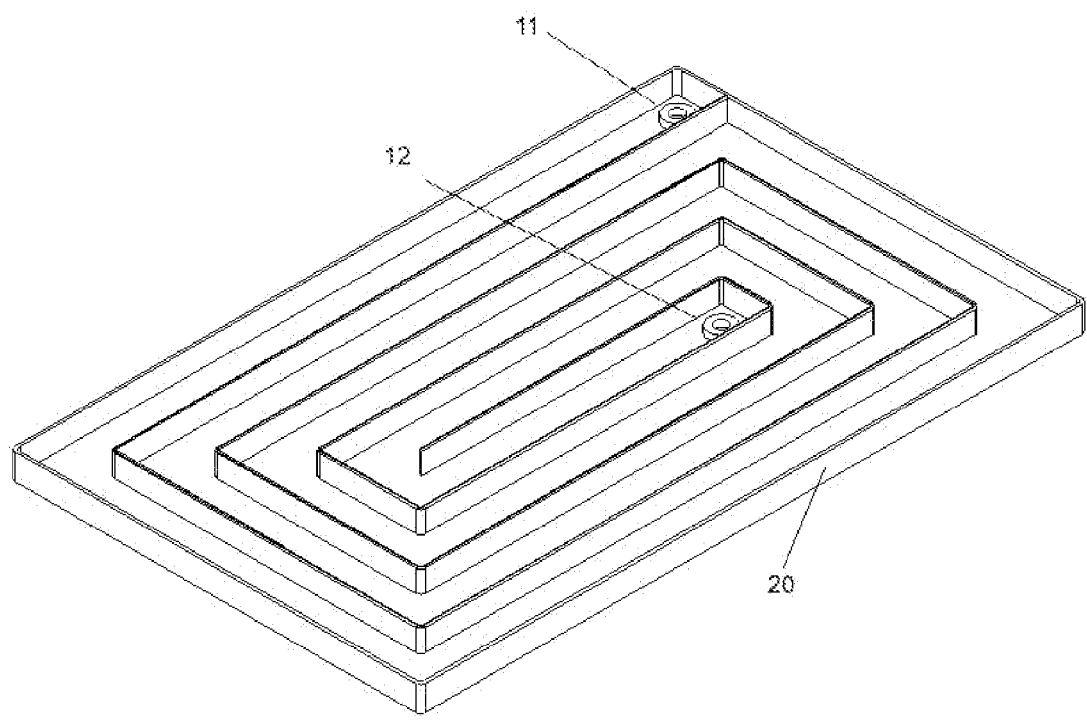
FIG. 9 is a perspective view of an exemplary plate of another rectangular embodiment of the invention.

The exemplary embodiment discussed above is a cylindrical culture chamber device that combines certain fluid/gas delivery and mixing conditions. The embodiment discussed above may incorporate uniquely designed fluid/air dams, and sloped inlet structures to enhance the delivery of fluid medium and gasses to each of the culture chambers. The fluid dams and sloped inlets may deliver gentle, low shear, fluid to the culture chambers. The low shear mixing may be desirous for the culture of cells and many of the biochemicals and proteins that may be subject to degradation caused by shear or denaturizing. However is will be understood by one skilled in the art, that other configurations may be constructed to achieve the same effects of mixing. Referring to FIGS. 8 and 9, the culture chambers 20 are illustrated with two different placements of the fluid inlet and outlet ports 11 and 12.

In another exemplary embodiment, the chambers may be molded to form a structure that is self-contained and fluid tight. The structure may be rendered fluid tight via sealing, molding or welding the chambers together. It should also be appreciated however that it may be desirable to separate the chambers to harvest the cells or products therein. Accordingly, the chamber may be designed to seal upon superimposing the cell growth chambers.

Figure 7:
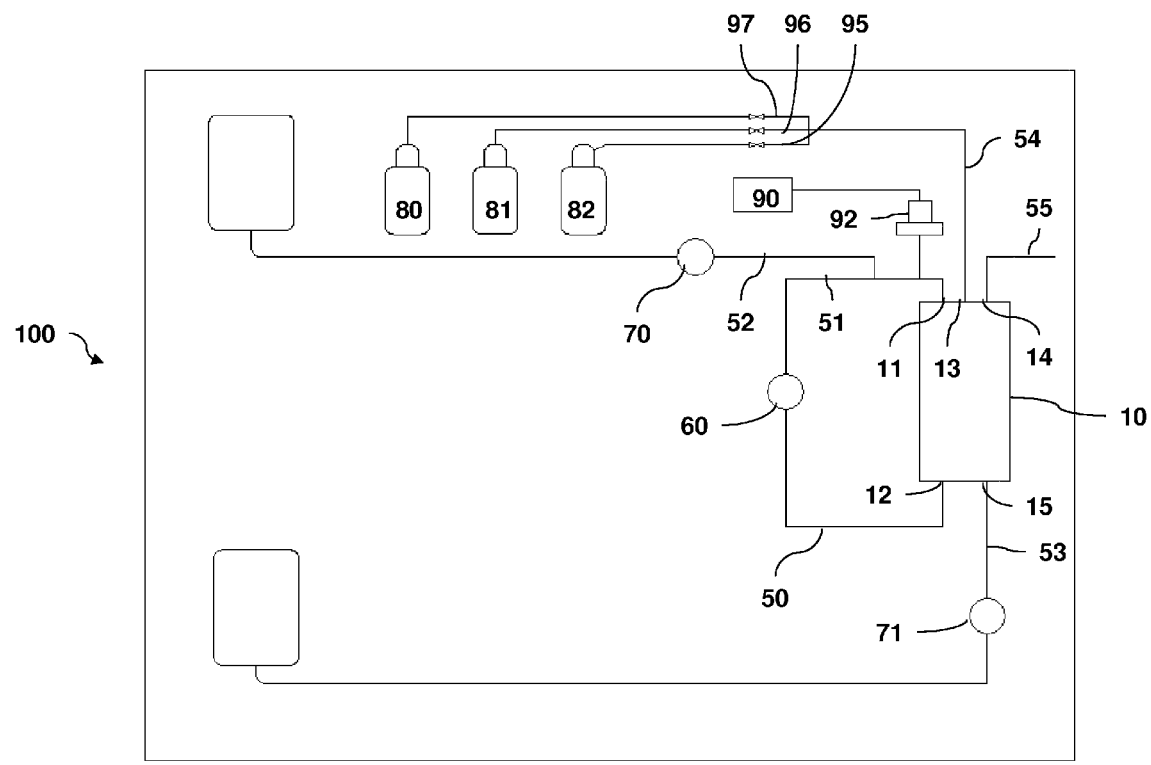
FIG. 7 is a schematic view of an embodiment of the invention incorporated into a continuous culture system.

According to one aspect of the invention, the cell culture device 10 may be provided as part of an assembly 100 as depicted schematically in reference to FIG. 7. The assembly 100 may be constructed and arranged for continuous operation. The assembly 100 may be a closed loop system connecting the culture vessel 10 of the invention into a continuous culture system.

The fluid collected in reservoir 26 may be delivered via the fluid outlet conduit 12 to conduit 50 and to pump 60. The pump 60 may move the fluid through conduit 51 to the fluid inlet conduit 11. Fresh nutrients may be added via pump 70 and conduit 52 to the fluid circulation in conduit 51. Excess nutrients-products/waste, may be collected by pump 71 via conduit 53 to maintain a constant volume of fluid within the vessel 10. Optional sensors 92 may be employed to monitor the system. The sensors 92 may be connected to a control means 90. The control means may have the ability to monitor or control the mixture of gasses delivered via conduit 54 to the gas inlet conduit 13 by controlling the gas mixture of gasses 80, 81 and 82 at valves 95, 96 and 97. The control means may have the ability to control the fluid input 70 and output 71 pumps and the circulation pump 60.

It should be understood that various changes and modifications of the embodiments described may be made within the scope of the invention. The foregoing description is provided to illustrate and explain the present invention. However, the description hereinabove should not be considered to limit the scope of the invention set forth in the claims appended here to.

What is claimed is:

1. A cell culture device comprising:
    a substantially cylindrical vessel, said vessel comprising:
        a plurality of serially connected cell growth chambers, the interior surfaces of said cell growth chambers adapted for the growth of cells and defining a culture space;
        a separate inlet defined in each of said cell growth chambers for providing fluid and gasses to said culture space; and
        a separate outlet defined in each of said cell growth chambers for collecting said fluid and gasses from said culture space, wherein said interior surfaces form a channel that is defined by a wall and a base located between said inlet and outlet,
        wherein said outlet of a prior cell growth chamber serially communicates with said inlet of a subsequent cell growth chamber, forming a serially connected culture space between said plurality of cell growth chambers
        wherein each of said plurality of cell growth chambers includes a fluid dam and a gas dam.

2. The cell culture device of claim 1 wherein said culture space is further defined by a plurality of superpositioned cell growth chambers in a stacked array, including a first cell growth chamber and a last cell growth chamber.

3. The cell culture device of claim 1 wherein each of said cell growth chambers includes a sloped inlet.

4. The cell culture device of claim 1 wherein the length of said culture space is defined by the distance between said inlet of said first cell growth chamber and said outlet of said last cell growth chamber.

5. The cell culture device of claim 4 wherein said device is sealed.

6. The cell culture device of claim 4 wherein said device is welded.

7. The cell culture device of claim 4 wherein said device is molded.

8. The cell culture device of claim 4 wherein said device includes a pump, wherein said pump circulates a nutrient medium.

9. The cell culture device of claim 1 wherein said cell growth chambers are stacked between a top plate and a reservoir, forming a self-contained, fluid tight device for said culture space.

10. The cell culture device of claim 1 wherein said plurality of cell growth chambers may be separated.

11. The cell culture device of claim 1 wherein said interior surfaces are modified to contain macro, micro or nano structures to enhance the attachment, distribution or mixing of the culture fluids and gasses.

* * * * *